United States Patent
Watanabe et al.

(10) Patent No.: US 9,420,985 B2
(45) Date of Patent: Aug. 23, 2016

(54) X-RAY DIAGNOSTIC APPARATUS AND DOSE DISTRIBUTION GENERATION METHOD

(71) Applicants: KABUSHIKI KAISHA TOSHIBA, Minato-ku (JP); Toshiba Medical Systems Corporation, Otawara-shi (JP)

(72) Inventors: Yuichiro Watanabe, Yaita (JP); Naotaka Sato, Otawara (JP); Shingo Abe, Nasushiobara (JP)

(73) Assignees: KABUSHIKI KAISHA TOSHIBA, Minato-ku (JP); Toshiba Medical Systems Corporation, Otawara-shi (JP)

( * ) Notice: Subject to any disclaimer, the term of this patent is extended or adjusted under 35 U.S.C. 154(b) by 163 days.

(21) Appl. No.: 14/451,734

(22) Filed: Aug. 5, 2014

(65) Prior Publication Data

US 2015/0071407 A1    Mar. 12, 2015

(30) Foreign Application Priority Data

Sep. 6, 2013    (JP) .................................. 2013-185585

(51) Int. Cl.
*G01N 23/04* (2006.01)
*A61B 6/00* (2006.01)

(52) U.S. Cl.
CPC .............. *A61B 6/5217* (2013.01); *A61B 6/5294* (2013.01); *A61B 6/542* (2013.01); *A61B 6/461* (2013.01); *A61B 6/544* (2013.01)

(58) Field of Classification Search
CPC .......... A61B 6/02; A61B 6/107; A61B 6/461; A61B 6/465; A61B 6/542; A61B 6/544; A61B 6/5217; A61B 6/5294; A61B 6/0407
See application file for complete search history.

(56) References Cited

U.S. PATENT DOCUMENTS

| | | | |
|---|---|---|---|
| 8,611,499 B2 | 12/2013 | Spahn | |
| 8,681,941 B2 * | 3/2014 | Bernhardt | A61B 6/542 378/97 |
| 2012/0150520 A1 | 6/2012 | Vaillant et al. | |
| 2013/0003915 A1 | 1/2013 | Lautenschlaeger et al. | |
| 2013/0243162 A1 | 9/2013 | Desponds et al. | |

OTHER PUBLICATIONS

F. Boujan, et al., "A new method of real time skin dose visualization: clinical evaluation of fluoroscopy guided interventions", ECR 2012, 11 pages.

\* cited by examiner

*Primary Examiner* — Courtney Thomas
(74) *Attorney, Agent, or Firm* — Oblon, McClelland, Maier & Neustadt, L.L.P.

(57) ABSTRACT

An X-ray diagnostic apparatus according to an embodiment includes a support mechanism, bed, dosimeter, dose decision unit, dose distribution generation unit and display unit. The support mechanism movably supports an X-ray tube generating X-rays over a plurality of times in a predetermined period and an X-ray detector detecting X-rays transmitted through an object. The bed includes a top on which the object is placed. The dosimeter measures a total dose over the period. The dose decision unit decides doses respectively corresponding to times of generation of the X-rays in the period based on the total dose and an X-ray irradiation condition. The dose distribution generation unit generates a dose distribution based on a position of the support mechanism, a position of the bed, and the doses. The display unit displays the dose distribution.

10 Claims, 11 Drawing Sheets

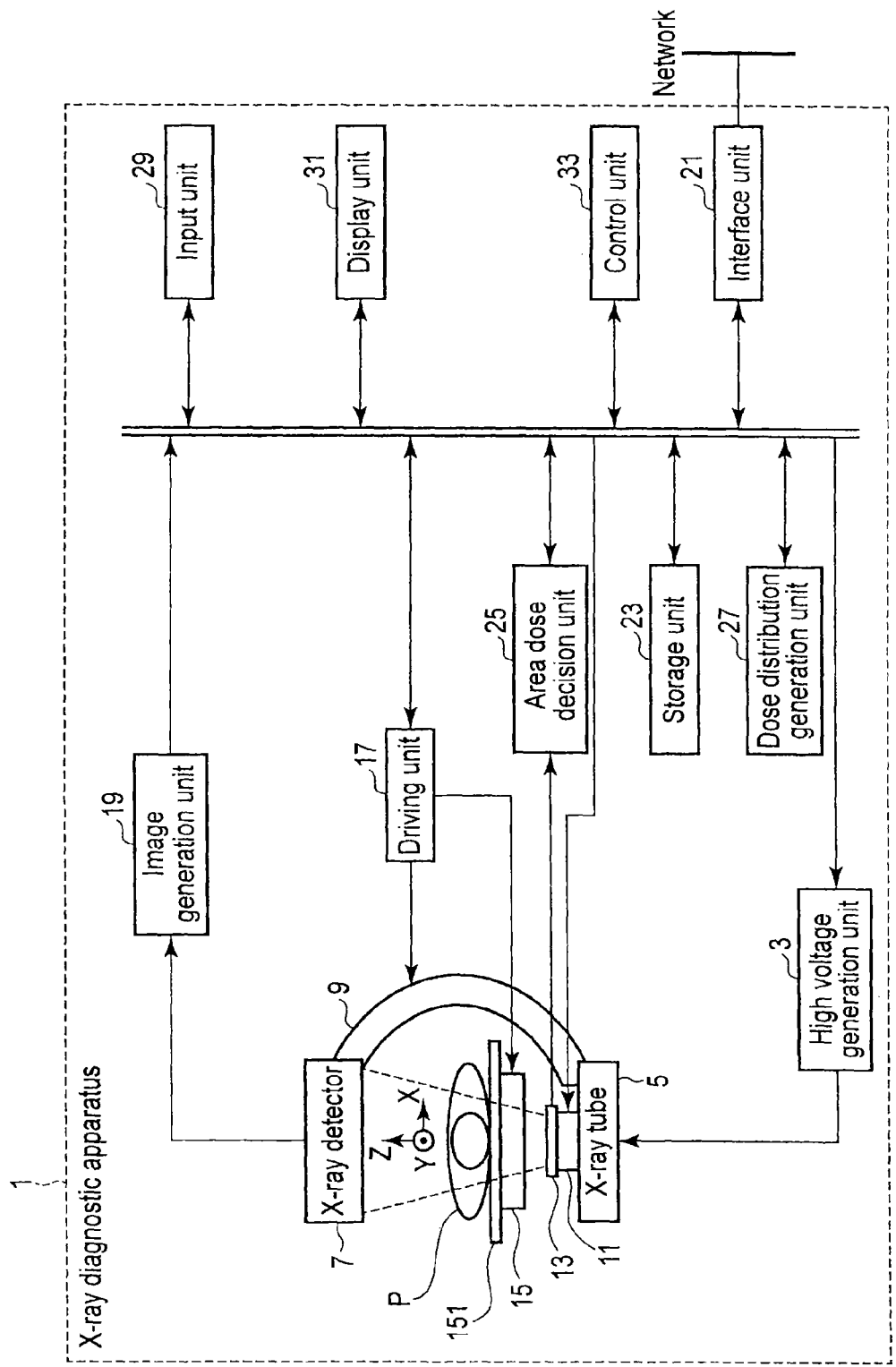
F I G. 1

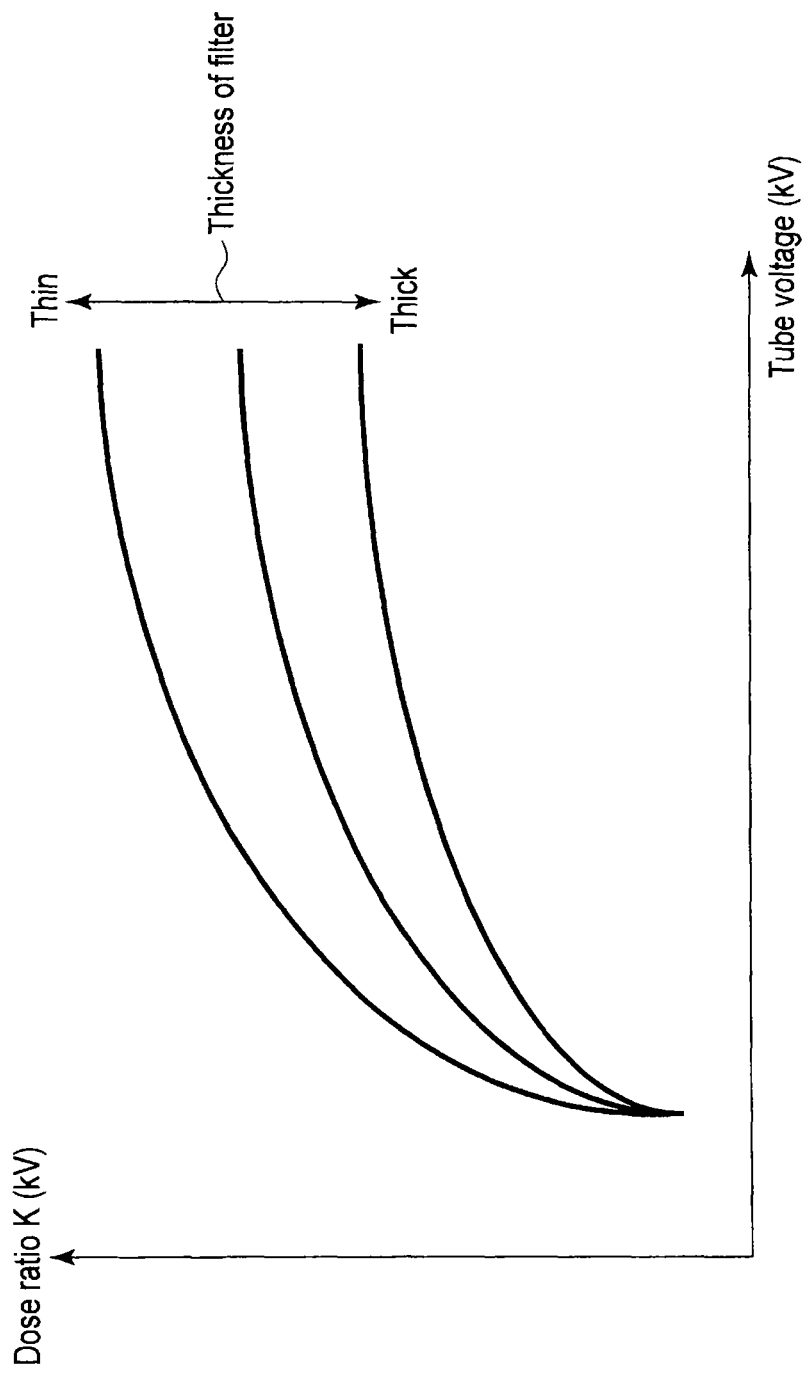
F I G. 4

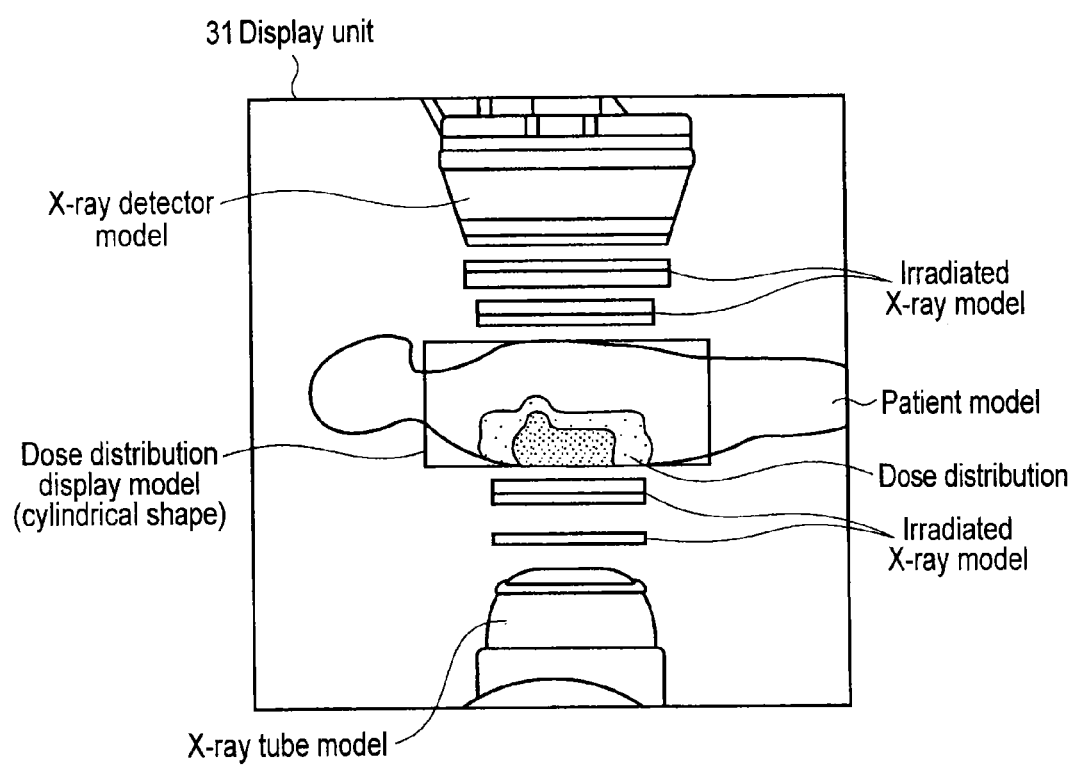
F I G. 10

X-RAY DIAGNOSTIC APPARATUS AND DOSE DISTRIBUTION GENERATION METHOD

CROSS-REFERENCE TO RELATED APPLICATIONS

This application is based upon and claims the benefit of priority from the prior Japanese Patent Application No. 2013-185585, filed Sep. 6, 2013, the entire contents of which are incorporated herein by reference.

FIELD

Embodiments described herein relate generally to an X-ray diagnostic apparatus and a dose distribution generation method.

BACKGROUND

Recently, in an X-ray diagnostic apparatus for circulatory organs, with increases in the number of examinations and treatment time in association with intervention, exposure of patients to X-rays poses a problem. For this reason, the X-ray diagnostic apparatus sometimes displays a reference air kerma as an index for the exposure dose to a patient, on the irradiation side of X-rays generated by an X-ray tube, based on an output from an area dosimeter. In addition, dose information based on DICOM RDSR (Radiation Dose Structure Report) is standardized and output to the outside. That is, the skin dose to the object is calculated based on an output from the area dosimeter.

However, the dose information using the output from the above area dosimeter represents a total dose but does not represent a PSD (Peak Skin Dose) as important dose information concerning the object. For this reason, a conventional X-ray diagnostic apparatus has a problem that it is not possible to accurately display a local exposure risk concerning an object. In order to solve this problem, the X-ray diagnostic apparatus has, for example, a dose map function of displaying a skin dose integration value estimated concerning an object on a patient model in color. In general, however, the dose map function also uses an output from the area dosimeter.

The area dosimeter has a problem that it can only acquire an integral area dose at predetermined time intervals due to a problem of output responsiveness. This makes it impossible to accurately acquire a dose for each time of X-ray irradiation to an object.

As described above, the X-ray diagnostic apparatus including the dose map function and the area dosimeter cannot accurately calculate a skin dose to an object when performing, for example, rotational imaging and panning operation in which an irradiation position changes during an irradiation period, and hence cannot generate a useful dose distribution as an index for exposure of the object.

BRIEF DESCRIPTION OF THE DRAWINGS

FIG. 1 is a block diagram showing an example of the arrangement of an X-ray diagnostic apparatus according to an embodiment.

FIG. 4 is a graph showing an example of the relationship between tube voltage (kV) and dose ratio K (kV) for each of the thicknesses of a plurality of filters according to this embodiment.

FIG. 10 is a view showing an example of the dose distribution displayed on the display unit together with a cylindrical dose distribution display model according to this embodiment.

DETAILED DESCRIPTION

Figure 2:
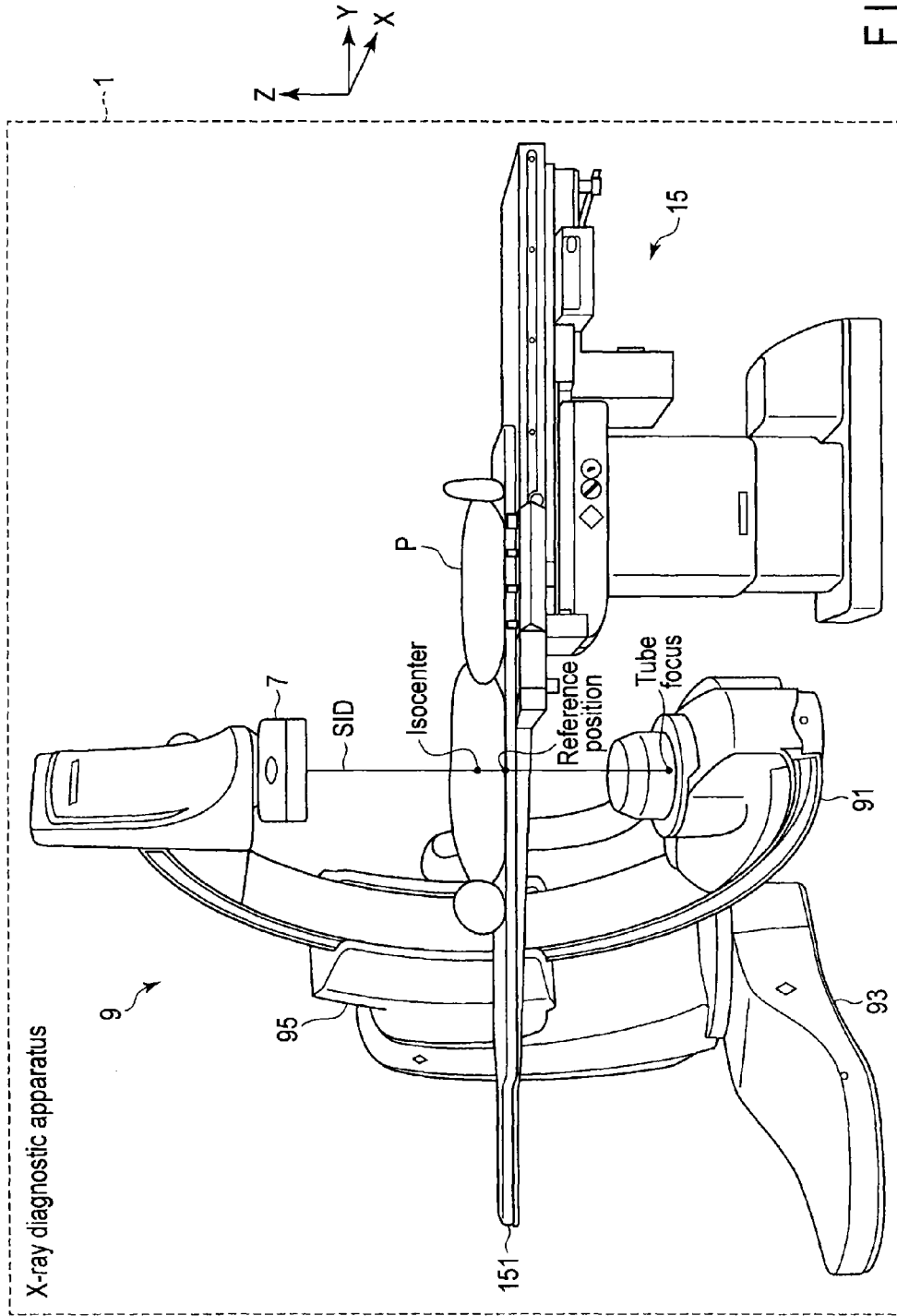
FIG. 2 is a perspective view showing the outer appearance of the X-ray diagnostic apparatus according to this embodiment.

In general, according to one embodiment, an X-ray diagnostic apparatus includes a support mechanism, a bed, a dosimeter, a dose decision unit, a dose distribution generation unit and a display unit. The support mechanism movably supports an X-ray tube generating X-rays over a plurality of times in a predetermined period and an X-ray detector detecting X-rays transmitted through an object. The bed includes a top on which the object is placed. The dosimeter measures a total dose over the period. The dose decision unit decides doses respectively corresponding to times of generation of the X-rays in the period based on the total dose and an X-ray irradiation condition. The dose distribution generation unit generates a dose distribution based on a position of the support mechanism, a position of the bed, and the doses. The display unit displays the dose distribution.

An X-ray diagnostic apparatus according to an embodiment will be described below with reference to the accompanying drawings. In the following description, the same reference numerals denote constituent elements having almost the same functions and arrangements, and a repetitive description will be made only when required.

FIG. 1 shows the arrangement of an X-ray diagnostic apparatus 1 according to this embodiment. The X-ray diagnostic apparatus 1 includes a high voltage generation unit 3, an X-ray tube 5, an X-ray detector 7, a support mechanism 9, an irradiation range limiter 11, a dosimeter 13, a bed 15 having a top 151, a driving unit 17, an image generation unit 19, an interface unit 21, a storage unit 23, an area dose decision unit (dose decision unit) 25, a dose distribution generation unit 27, an input unit 29, a display unit 31, and a control unit 33. FIG. 2 is a perspective view showing the outer appearance of the X-ray diagnostic apparatus 1 according to the embodiment.

The high voltage generation unit 3 generates a tube current to be supplied to the X-ray tube 5 and a tube voltage to be applied to the X-ray tube 5. The high voltage generation unit 3 supplies tube currents respectively suitable for X-ray imaging and X-ray fluoroscopy to the X-ray tube 5 and applies tube voltages respectively suitable for X-ray imaging and X-ray fluoroscopy to the X-ray tube 5 in accordance with X-ray irradiation conditions (to be described later) under the control of the control unit 33 (to be described later).

For example, when performing X-ray fluoroscopy with respect to an object P, the high voltage generation unit 3 applies a tube voltage to the X-ray tube 5 and supplies a tube current to the X-ray tube 5 a plurality of times in a dose measurement period of the dosimeter 13 (to be described later). The time during which the object P is irradiated with X-rays in a dose measurement period will be referred to as an irradiation time hereinafter. In addition, the intervals at which the object P is irradiated with X-rays in a dose measurement period will be referred to as irradiation intervals.

The X-ray tube 5 generates X-rays from an X-ray focus (to be referred to as a tube focus hereinafter) based on the tube current supplied from the high voltage generation unit 3 and the tube voltage applied from the high voltage generation unit 3. The object P is irradiated with the X-rays generated from the tube focus via an X-ray radiation window provided on the front surface of the X-ray tube 5.

The X-ray detector 7 detects the X-rays generated from the X-ray tube 5 and transmitted through the object P. For example, the X-ray detector 7 includes an FPD (Flat Panel Detector). The FPD includes a plurality of semiconductor detection elements. A semiconductor detection element includes a direct conversion type and an indirect conversion type. The direct conversion type is a form of directly converting incident X-rays into an electrical signal. The indirect conversion type is a form of converting incident X-rays into light via a phosphor and converting the light into an electrical signal.

The electrical signals generated by a plurality of semiconductor detection elements upon entrance of X-rays are output to an analog to digital converter (to be referred to as an A/D converter hereinafter) (not shown). The A/D converter converts an electrical signal into digital data. The A/D converter outputs the digital data to a preprocessing unit (not shown). Note that an image intensifier may be used as the X-ray detector 7.

The support mechanism 9 movably supports the X-ray tube 5 and the X-ray detector 7. More specifically, the support mechanism 9 includes a C-arm 91 and a C-arm support portion 93 in FIG. 2. The X-ray tube 5 and the X-ray detector 7 are mounted on the C-arm 91 so as to face each other. Note that an Ω arm may be used in place of the C-arm 91. The C-arm support portion 93 slidably supports the C-arm 91 in a direction along the C shape of the C-arm (to be referred to as the first direction hereinafter).

In addition, the C-arm support portion 93 supports the C-arm 91 so as to make it rotatable in a direction (to be referred to as the second direction hereinafter) perpendicular to the first direction about a connecting portion 95 connecting the C-arm 91 to the C-arm support portion 93. Note that the C-arm support portion 93 can also support the C-arm 91 so as to allow it to translate in the short-axis direction (the X direction in FIGS. 1 and 2) and the long-axis direction (the Y direction in FIGS. 1 and 2) of the top 151 (to be described later). In addition, the C-arm 91 supports the X-ray tube 5 and the X-ray detector 7 such that it is possible to change the distance (to be referred to as the SID (Source Image Distance) hereinafter) between tube focus of the X-ray tube 5 and the X-ray detector 7.

Note that the support mechanism 9 of the X-ray diagnostic apparatus 1 according to this embodiment is not limited to the structure formed by the C-arm 91. For example, the support mechanism 9 may be supported so as to be movable in an arbitrary direction by two arms (for example, robot arms) which respectively support the X-ray tube 5 and the X-ray detector 7. In addition, the support mechanism 9 may be an Ω arm suspended from the ceiling in place of the C-arm 91. The support mechanism 9 may also have a biplane structure. The support mechanism 9 in the X-ray diagnostic apparatus 1 according to this embodiment is not limited to the over tube system, the under tube system, or the like but may be applied to an arbitrary form.

The irradiation range limiter 11 is provided on the front surface of the X-ray radiation window of the X-ray tube 5. That is, the irradiation range limiter 11 is provided between the X-ray tube 5 and the X-ray detector 7 (to be described later). The irradiation range limiter 11 is also called an X-ray movable stop. More specifically, the irradiation range limiter 11 limits an irradiation range having a maximum aperture (to be referred to as a maximum irradiation range hereinafter) in accordance with an irradiation area on the body surface of the object P which is irradiated with X-rays, in order to prevent any region other than the imaging region desired by an operator from being exposed to the X-rays generated from the tube focus. For example, the irradiation range limiter 11 limits an irradiation range by moving stop blades in accordance with an instruction to limit an irradiation range which is input via the input unit 29 (to be described later).

More specifically, the irradiation range limiter 11 includes a plurality of first stop blades movable in a predetermined direction and a plurality of second stop blades movable in a direction different from the predetermined direction. The first and second stop blades are formed from lead which shields X-rays generated from the tube focus.

Note that the irradiation range limiter 11 may include a plurality of predetermined filters (to be referred to as radiation quality adjustment filters hereinafter) to be inserted into an X-ray irradiation field to reduce the exposure dose to the object P and improve image quality. The plurality of radiation quality adjustment filters respectively have different thicknesses. Note that the radiation quality adjustment filters may be respectively formed from different materials and have the same thickness. The radiation quality adjustment filters change the radiation quality of X-rays generated from the tube focus in accordance with the thicknesses. The radiation quality adjustment filters are made of, for example, aluminum or copper. The operator selects one of the radiation quality adjustment filters via the input unit 29 in accordance with an imaging plan for the object P. The radiation quality adjustment filter selected from the plurality of radiation quality adjustment filters is inserted into the X-ray irradiation field of the irradiation range limiter 11 under the control of the control unit 33 (to be described later).

Each radiation quality adjustment filter reduces low-energy X-ray components (soft X-ray components), of the X-rays generated from the tube focus (to be referred to as generated X-rays hereinafter), which can be easily absorbed by the object P. Alternatively, the radiation quality adjustment filter may reduce high-energy X-ray components, of the generated X-rays, which cause a decrease in contrast, on the medical image generated by the image generation unit 19 (to be described later).

The dosimeter 13 is provided on the front surface of the irradiation range limiter. That is, the dosimeter 13 is provided between the irradiation range limiter 11 and the X-ray detector 7. The dosimeter 13 is, for example, an area dosimeter. The dosimeter 13 measures the integration value of area doses (to be referred to as a total area dose (total dose)) over a predetermined period. The predetermined period is a dose measurement period. The dose measurement period corresponds to a readout period (to be referred to as a dose readout period hereinafter) during which the total area dose measured by the dosimeter 13 is read out from the area dosimeter. The dosimeter 13 outputs the total area dose read out for each dose readout period to the area dose decision unit 25 (to be described later) and the storage unit 23.

Figure 3:
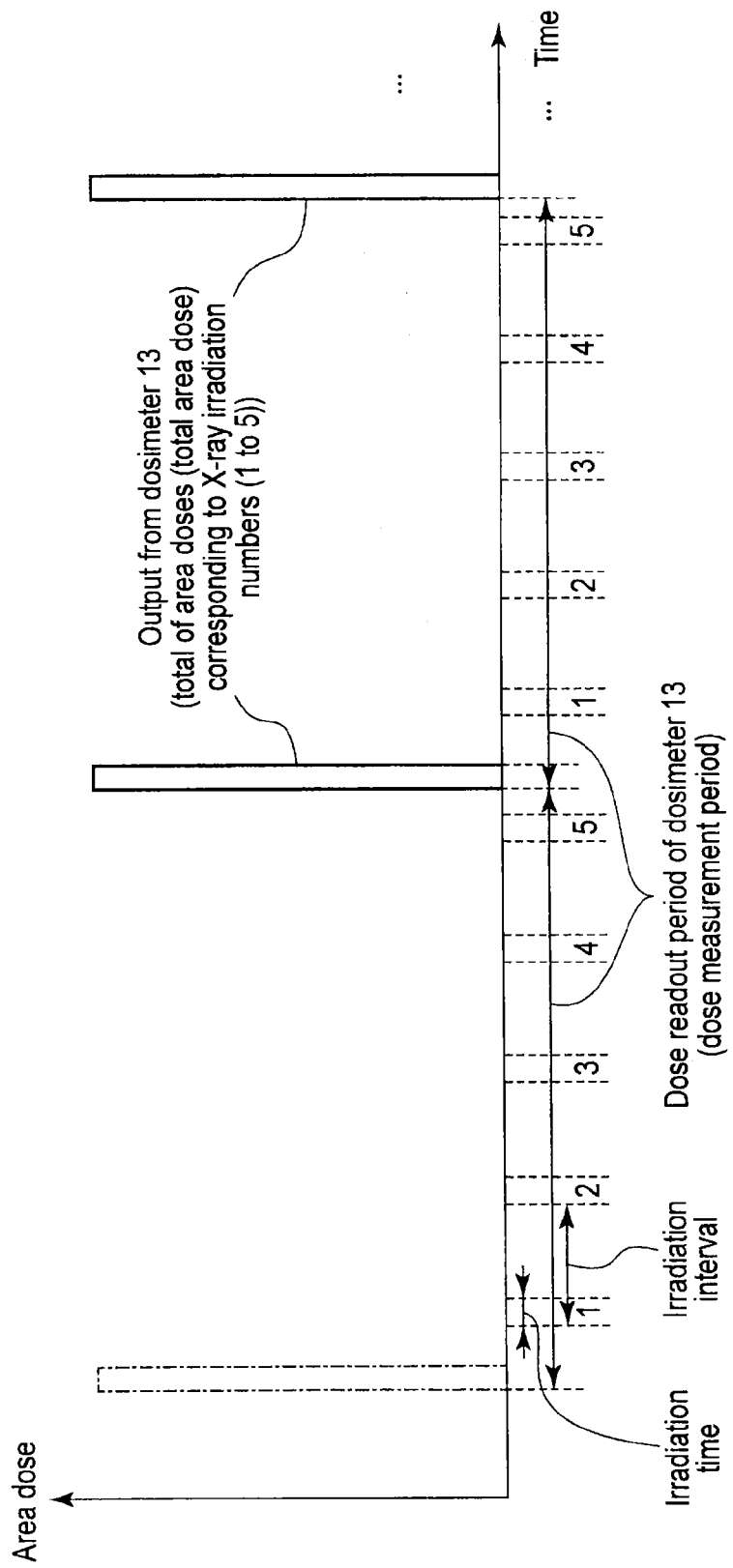
FIG. 3 is a graph showing the dose readout period of a dosimeter, together with the total area dose read out from the dosimeter, the irradiation time, and the irradiation interval, according to this embodiment.

FIG. 3 is a graph showing the dose readout period of the dosimeter 13, together with the total area dose read out from the dosimeter 13, the irradiation time, and the irradiation interval. For the sake of simplicity, assume that the number of times of X-ray irradiation (to be referred to as an irradiation count hereinafter) to the object P in a dose readout period is five. Note that the irradiation count is not limited to five and may be an arbitrary count equal to or more than two.

The bed 15 includes the top 151 (to be also referred to as a supine table) on which the object P is placed. The object P is placed on the top 151.

The driving unit 17 drives the support mechanism 9 and the bed 15 under the control of the control unit 33 (to be described later). More specifically, the driving unit 17 slides the C-arm 91 in the first direction and rotates the C-arm 91 in the second direction (CRA or CAU) by supplying a driving signal corresponding to a control signal from the control unit 33 (to be described later) to the C-arm support portion 93. At the time of X-ray fluoroscopy or X-ray imaging, the object P placed on the top 151 is arranged between the X-ray tube 5 and the X-ray detector 7. The driving unit 17 outputs the position of the X-ray tube 5 (or the position of the support mechanism 9) relative to the top 151 to the dose distribution generation unit 27 (to be described later), the storage unit 23, and the like.

The driving unit 17 moves the top 151 by driving the top 151 under the control of the control unit 33 (to be described later). More specifically, the driving unit 17 slides the top 151 in the short-axis direction (the X direction in FIGS. 1 and 2) of the top 151 or the long-axis direction (the Y direction in FIGS. 1 and 2) of the top 151, based on a control signal from the control unit 33. In addition, the driving unit 17 moves the top 151 up and down in the vertical direction (the Z direction in FIGS. 1 and 2). In addition, the driving unit 17 may rotate the top 151 in at least one of the long-axis direction and the short-axis direction as a rotation axis (the X-axis or the Y-axis in FIG. 1) in order to tilt the top 151. The driving unit 17 outputs the position of the top 151 to the dose distribution generation unit 27 (to be described later).

The driving unit 17 outputs the relative positional relationship between the X-ray tube 5 and the top 151 to the dose distribution generation unit 27 (to be described later). The relative positional relationship between the X-ray tube 5 and the top 151 is associated with, for example, the angle (tilt) of the C-arm 91 relative to the top 151, the sliding angle of the C-arm 91 (called the arm angle), and the like. The tilt or the arm angle is the Euler angle with reference to the isocenter relative to the object. Note that the driving unit 17 may drive the X-ray detector 7 to arbitrarily rotate it in accordance with the position of the support mechanism 9, the angle of the C-arm 91, or the like.

A preprocessing unit (not shown) executes preprocessing for the digital data output from the X-ray detector 7. Preprocessing includes correction of sensitivity unevenness between the channels in the X-ray detector 7 and correction concerning an excessive decrease in signal level or data omission due to an X-ray absorber such as a metal. The preprocessed digital data is output to the image generation unit 19 (to be described later).

The image generation unit 19 generates a captured image based on preprocessed digital data after X-ray imaging at an imaging position. The image generation unit 19 generates a fluoroscopic image based on preprocessed digital data after X-ray fluoroscopy at a fluoroscopy position. Captured images and fluoroscopic images will be collectively referred to as projection images hereinafter. The image generation unit 19 outputs the generated projection image to the display unit 31 (to be described later) and the storage unit 23.

The interface unit 21 is, for example, an interface for a network and an external storage device (not shown). Data such as a projection image obtained by the X-ray diagnostic apparatus 1, an analysis result, and the like can be transferred to another medical apparatus via the interface unit 21 and the network.

The storage unit 23 stores various types of projection images generated by the image generation unit 19, control programs for the X-ray diagnostic apparatus 1, a diagnosis protocol, the instruction issued by the operator and sent from the input unit 29 (to be described later), various types of data groups such as imaging conditions and fluoroscopy conditions, various types of data sent via the interface unit 21 and a network, a total area dose, and the like. The storage unit 23 may also store the relative positional relationship between the X-ray tube 5 and the top 151.

More specifically, the storage unit 23 stores X-ray irradiation conditions for each time of X-ray irradiation (generation) to an object. X-ray irradiation conditions include conditions associated with radiation quality (a tube voltage, tube current, and the like), an irradiation time, an irradiation interval, the aperture of the irradiation range limiter 11, the product (to be referred to as a tube current time product (mAs) hereinafter) of a tube current (mA) and an irradiation time (s), the thickness of the radiation quality adjustment filter (or the type of radiation quality adjustment filter) selected via the input unit 29, an X-ray irradiation (generation) count in a dose measurement period, an FOV (Field Of View), and an irradiation rate (X-ray irradiation count per sec). The X-ray irradiation conditions are changed as needed in accordance with the thickness of an object concerning an imaging region. Of the X-ray irradiation conditions, the thickness (type) of the radiation quality adjustment filter, the irradiation time, the irradiation rate, and the like are set in advance as needed by the input unit 29 (to be described later).

The storage unit 23 stores geometrical conditions for each time of X-ray irradiation (generation) to an object. The geometrical conditions include a predetermined reference position, the position of the top 151, the position of the C-arm 91, the angle of the C-arm 91, SID, and FPD rotational angle. The predetermined reference position is, for example, a position 15 cm away from the isocenter of the X-ray diagnostic apparatus 1 toward the tube focus. Note that the storage unit 23 may store a correspondence table between the reference position and the irradiation area at the reference position for an aperture. The storage unit 23 also stores an irradiation area for each time of X-ray irradiation.

The storage unit 23 stores a patient model to be used by the dose distribution generation unit 27 (to be described later). Note that the storage unit 23 may also store a dose distribution generation program for generating a dose distribution at a predetermined reference position. The storage unit 23 also stores the dose distribution generated by the dose distribution generation unit 27. Note that the storage unit 23 may store X-ray irradiation conditions, geometrical conditions, and a dose distribution in accordance with each of a plurality of times of X-ray generation (irradiation) over a dose measurement period, and may update and store the X-ray irradiation conditions, the geometrical conditions, and the dose distribution for each dose measurement period.

The storage unit 23 may also store X-ray irradiation conditions and geometrical conditions as an irradiation history for each time of X-ray irradiation. The storage unit 23 stores the relationship between dose ratios K (kV) and tube voltages (kV) respectively corresponding the thicknesses (or types) of a plurality of radiation quality adjustment filters.

The area dose decision unit 25 decides a plurality of area doses (doses) respectively corresponding to a plurality of times of X-ray irradiation (generation) in a dose readout period based on a total area dose and X-ray irradiation conditions. That is, the area dose decision unit 25 decides an area dose for each total area dose output (for each dose measurement period). The area dose decision unit 25 outputs a plurality of decided area doses to the dose distribution generation unit 27 together with corresponding irradiation areas.

More specifically, the area dose decision unit 25 reads out X-ray irradiation conditions from the storage unit 23. The area dose decision unit 25 decides an irradiation area at a reference position based on the aperture and the reference position. Note that the area dose decision unit 25 may decide an irradiation area based on the aperture and the correspondence table.

The area dose decision unit 25 then decides a unit tube current time product and a dose per unit area (to be referred to as a dose ratio K hereinafter) based on the thickness of the radiation quality adjustment filter (or the type of radiation quality adjustment filter) and tube voltage of the X-ray irradiation conditions. In general, a tube voltage is not proportional to a dose. For this reason, in order to make a tube voltage proportional to a dose, a predetermined transformation is required. The dose ratio K obtained by transforming the tube voltage by the predetermined transformation is proportional to the dose.

FIG. 4 is a graph showing an example of the relationship (to be referred to as the tube voltage/dose ratio relationship hereinafter) between tube voltage (kV) and dose ratio K (kV) for each of the thicknesses of a plurality of predetermined filters (radiation quality adjustment filters). As shown in FIG. 4, the relationship between tube voltage and dose ratio K depends on the thickness of the radiation quality adjustment filter inserted into the X-ray irradiation field of the irradiation range limiter 11. That is, as the thickness of a radiation quality adjustment filter decreases, the inclination of the tube voltage/dose ratio relationship increases, as shown in FIG. 4. In addition, as the thickness of the radiation quality adjustment filter increases, the inclination of the tube voltage/dose ratio relationship decreases, as shown in FIG. 4.

The area dose decision unit 25 decides the rates (to be referred to as area dose rates (dose rates) hereinafter) of a plurality of area doses to a total area dose for each dose measurement period based on dose ratios, a tube current time product, and an irradiation area. More specifically, the area dose decision unit 25 calculates an integration value in a dose measurement period by integrating the multiplication values of the dose ratios K, tube current time products, and irradiation areas over a plurality of times of X-ray generation in the dose measurement period. The area dose decision unit 25 then calculates an area dose rate by dividing each of a plurality of multiplication values concerning X-ray irradiation (generation) by the integration value.

For example, in a dose measurement period, letting $K_i$ be the dose ratio K at the ith iteration of X-ray generation, $mAs_i$ be a tube current time product, and $S_i$ be an irradiation area, a multiplication value at the ith iteration of X-ray generation is given by $K_i \times mAs_i \times S_i$. In addition, letting n be the number of times of X-ray generation (irradiation) in the dose measurement period, an integration value is given by $\Sigma_{i=1}^{n}(K_i \times mAs_i \times S_i)$. An area dose rate is calculated according to $(K_i \times mAs_i \times S_i)/\{\Sigma_{i=1}^{n}(K_i \times mAs_i \times S_i)\}$. For the sake of simplicity, assume that the number of times of X-ray generation (irradiation) in a dose measurement period is five (n=5).

With the above calculation, the area dose decision unit 25 decides a plurality of area doses in the dose measurement period by multiplying each of a plurality of area dose rates respectively corresponding to a plurality of times of X-ray generation by the total area dose. That is, an area dose corresponding to the ith iteration of X-ray generation in the dose measurement period is decided by multiplying $(K_i \times mAs_i \times S_i)/\{\Sigma_{i=1}^{n}(K_i \times mAs_i \times S_i)\}$ by the total area dose. With the above operation, the area dose decision unit 25 can divide the total area dose in the dose measurement period into area doses for the respective times of X-ray generation (irradiation) in the dose measurement period.

Figure 5:
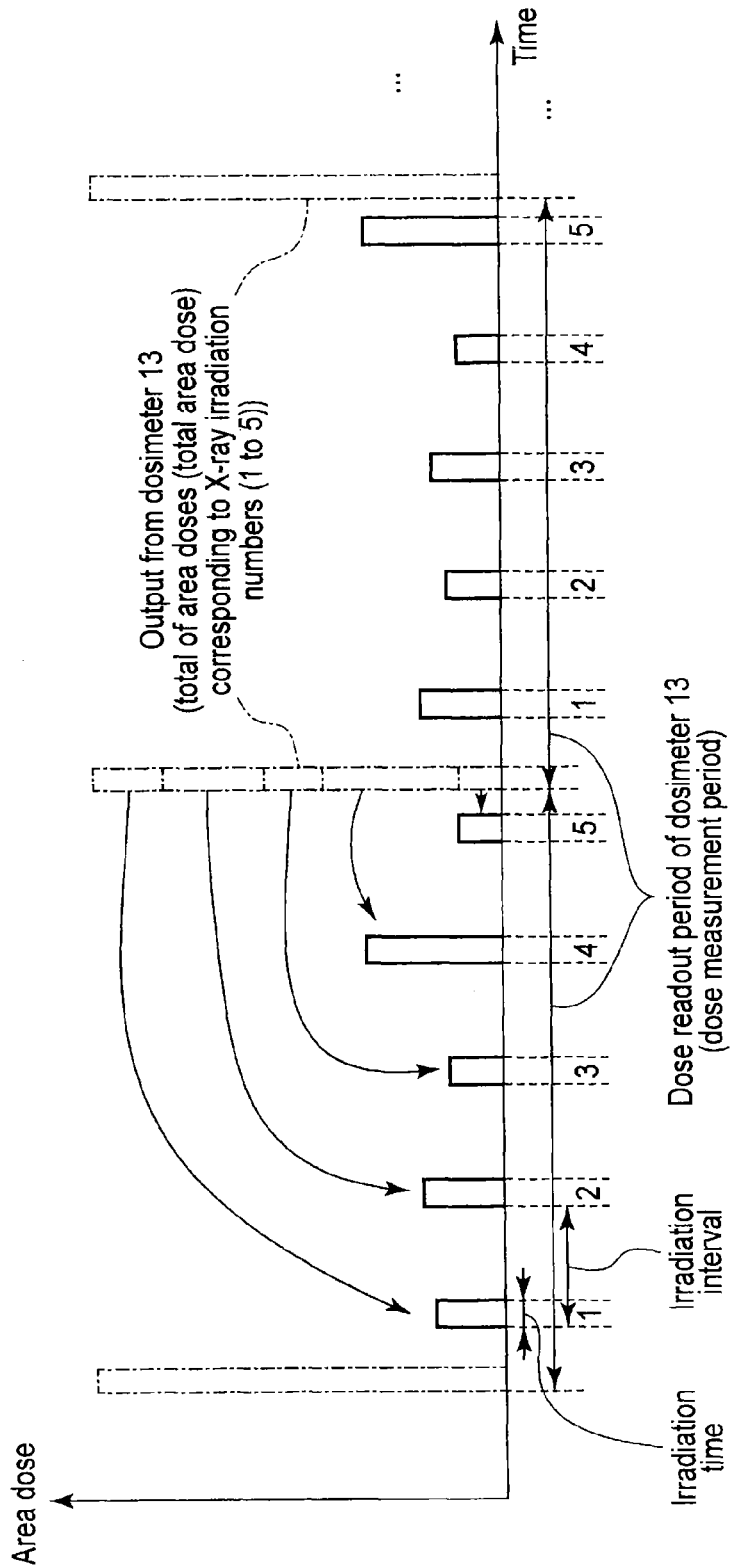
FIG. 5 is a graph showing an example obtained by dividing a total area dose into area doses for the respective times of X-ray generation (irradiation) of X-rays in a dose measurement period according to this embodiment.

FIG. 5 is a graph showing an example obtained by dividing a total area dose into area doses for the respective times of X-ray generation (irradiation) in a dose measurement period. As shown in FIG. 5, the total area dose in the dose measurement period is divided into area doses for the respective times of X-ray generation (irradiation) in the dose measurement period.

If different imaging regions are set for the respective times of X-ray irradiation, different area doses are set as shown in, for example, FIG. 5. Differences in area dose for the respective times of X-ray irradiation originate from differences in X-ray irradiation conditions because of differences in the thickness of the object between the respective imaging regions. Note that if the same imaging region is set for the respective times of X-ray irradiation, the area doses for the respective times of X-ray irradiation are almost equal to each other unlike the case of FIG. 5. The near equivalence of area doses is attributed to that, for example, X-ray irradiation conditions and geometrical conditions are almost the same for the respective times of X-ray irradiation.

When a total area dose is output for each dose measurement period, the area dose decision unit 25 divides the output total area dose into area doses for the respective times of X-ray irradiation. The area dose decision unit 25 outputs the area doses divided for each dose measurement period to the dose distribution generation unit 27 (to be described later). Note that the area dose decision unit 25 may decide an area dose for each time of X-ray irradiation based on an irradiation history and a total area dose.

The dose distribution generation unit 27 generates a dose distribution at a predetermined reference position based on the position of the support mechanism 9, the position of the bed 15, a plurality of area doses, and an irradiation area. More specifically, the dose distribution generation unit 27 generates a dose distribution based on a plurality of area doses, an irradiation area, the position of the support mechanism, and a relative positional relationship. That is, the dose distribution generation unit 27 generates a dose distribution for each dose measurement period.

If a dose distribution is stored in the storage unit 23, the dose distribution generation unit 27 generates a dose distribution by adding the generated dose distribution to the stored dose distribution. With this operation, the dose distribution generation unit 27 updates a dose distribution for each total area dose output (for each dose measurement period). The dose distribution generation unit 27 outputs the dose distribution to the display unit 31 (to be described later) and the storage unit 23.

More specifically, the dose distribution generation unit 27 calculates an air kerma at the reference position based on the position of the support mechanism 9, a relative positional relationship (geometrical conditions), a plurality of area doses, and an irradiation area. The dose distribution generation unit 27 reads out a patient model from the storage unit 23. The dose distribution generation unit 27 calculates a dose (patient skin dose) at an irradiation position on the patient model based on the calculated air kerma, the irradiation area, the position of the support mechanism 9, and the relative positional relationship (geometrical conditions).

Note that when calculating a patient skin dose from an air kerma, the dose distribution generation unit 27 can also calculate the patient skin dose in consideration of the influence of backscattered radiation. The dose distribution generation unit 27 generates a dose distribution by mapping the patient skin dose at the irradiation position on the patient model.

The input unit 29 inputs X-ray irradiation conditions such as X-ray imaging conditions and X-ray fluoroscopy conditions desired by the operator, a fluoroscopy/imaging position, an irradiation range, and the like. More specifically, the input unit 29 inputs various types of instruction, commands, information, selections, and settings from the operator to the X-ray diagnostic apparatus 1. A fluoroscopy/imaging position is defined by, for example, an angle relative to the isocenter. For example, if the starting point in the first oblique direction (RAO), second oblique direction (LAO), cranial direction (CRA), and caudal direction (CAU) is the fluoroscopy/imaging position and the origin of the three orthogonal axes in FIG. 2 is the isocenter, the fluoroscopy position angle at the starting point is 0°.

The input unit 29 includes a trackball, switch buttons, mouse, and keyboard for, for example, setting a region of interest. The input unit 29 detects the coordinates of the cursor displayed on a display screen and outputs the detected coordinates to the control unit 33 (to be described later). Note that the input unit 29 may be a touch panel provided to cover the display screen. In this case, the input unit 29 detects a touched and designated coordinates by a coordinate reading principle such as an electromagnetic induction scheme, magnetostriction scheme, or a pressure-sensitive scheme, and outputs the detected coordinates to the control unit 33.

The display unit 31 displays the projection image generated by the image generation unit 19. The display unit 31 displays the dose distribution generated by the dose distribution generation unit 27, together with the patient model. More specifically, the display unit 31 displays a superimposed image obtained by superimposing the dose distribution on the patient model. Note that the display unit 31 may display an input screen concerning the input of a fluoroscopy/imaging position, X-ray irradiation conditions, and the like.

Note that the display unit 31 may display the dose distribution on a model indicating a cylindrical dose distribution display area (to be referred to as a dose distribution display model hereinafter). The dose distribution display model is not limited to a cylindrical shape but may have an arbitrary stereoscopic shape (e.g., a cubic shape). For example, the cylindrical dose distribution display model is displayed so as to cover the patient model. In this case, the display unit 31 displays the X-ray irradiation range and the dose distribution on the surface of the cylindrical shape. Alternatively, the display unit 31 may display a model having a predetermined shape corresponding to an imaging region as a dose distribution display model in place of the patient model. The predetermined shape is, for example, a spherical shape when the imaging region is a head region. In addition, the predetermined shape is, for example, a cylindrical shape when the imaging region is an abdominal region. In this case, the display unit 31 displays the X-ray irradiation range and the dose distribution on the surface of the predetermined shaped.

The control unit 33 includes a CPU (Central Processing Unit) and a memory (neither of which is shown). The control unit 33 temporarily stores, in the memory (not shown), information such as operator instructions and X-ray irradiation conditions including imaging conditions and fluoroscopy conditions sent from the input unit 29. The control unit 33 controls the high voltage generation unit 3, the X-ray detector 7, the irradiation range limiter 11, and the driving unit 17 to execute X-ray imaging in accordance with the operator instructions, the fluoroscopy/imaging position, the X-ray irradiation conditions, and the like stored in the memory. The control unit 33 controls the high voltage generation unit 3, the X-ray detector 7, the irradiation range limiter 11, and the driving unit 17 to execute X-ray fluoroscopy in accordance with the operator instructions, the fluoroscopy conditions, and the like stored in the memory.

The control unit 33 reads out a dose distribution generation program stored in the storage unit 23 and loads the program in the memory. The control unit 33 controls the area dose decision unit 25, the dose distribution generation unit 27, the display unit 31, and the like in accordance with the dose distribution generation program loaded in the memory.

(Dose Distribution Generation Function)

The dose distribution generation function is a function of deciding a plurality of area doses respectively corresponding to a plurality of times of X-ray irradiation (generation) in a dose measurement period based on a total area dose and X-ray irradiation conditions and generating and displaying a dose distribution at the reference position based on the plurality of decided area doses, geometrical conditions, and an irradiation area. Processing concerning the dose distribution generation function (to be referred to as dose distribution generation processing hereinafter) will be described below.

Figure 6:
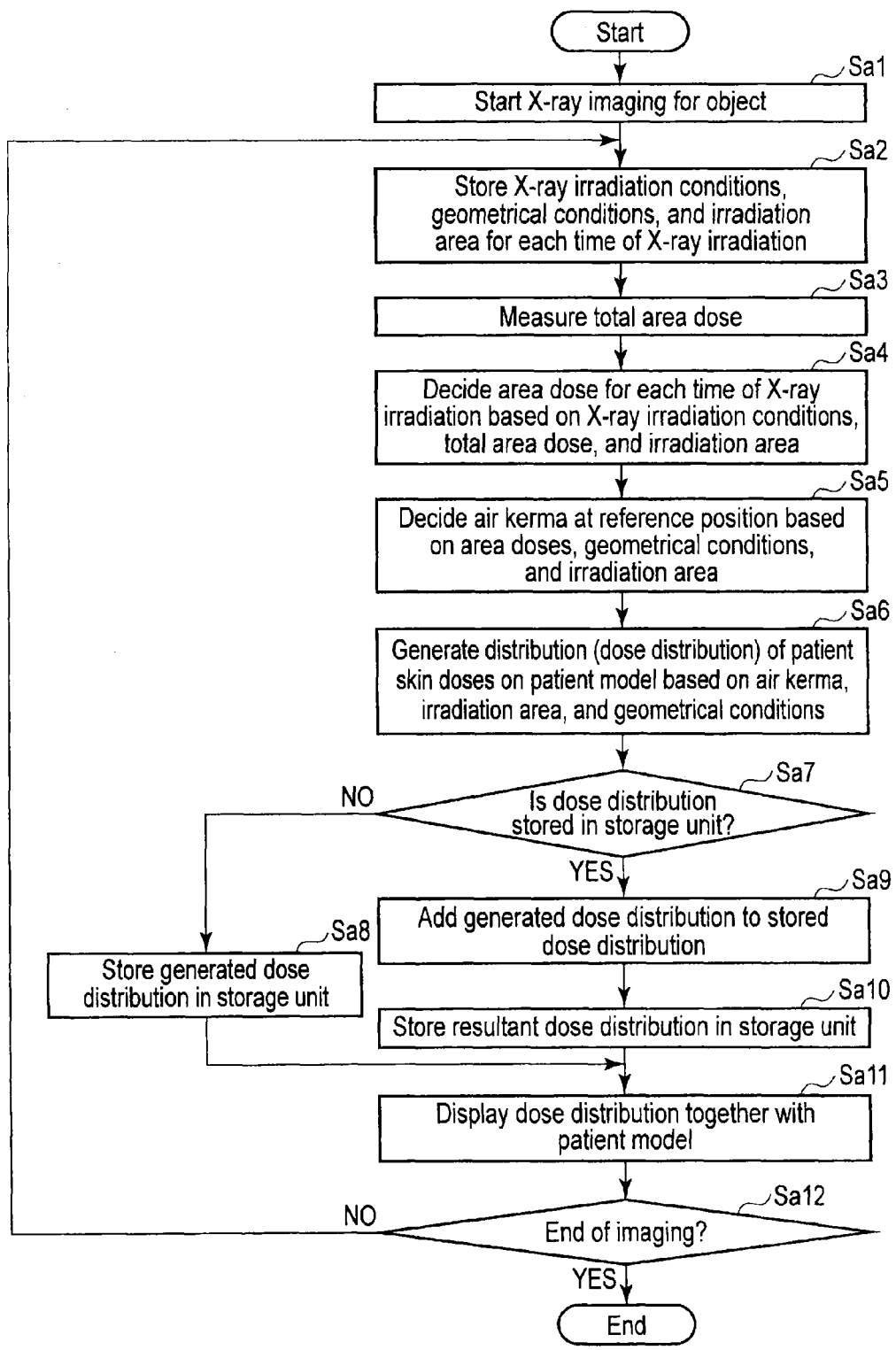
FIG. 6 is a flowchart showing an example of dose distribution generation processing according to this embodiment.

FIG. 6 is a flowchart showing an example of a procedure for dose distribution generation processing.

X-ray imaging is started for an object (step Sa1). The storage unit 23 stores X-ray irradiation conditions, geometrical conditions, and an irradiation area for each time of X-ray irradiation to the object (step Sa2). A total area dose is measured (step Sa3). An area dose for each time of X-ray irradiation is decided based on the X-ray irradiation conditions, the total area dose, and the irradiation area (step Sa4). An air kerma at the reference position is decided based on the area doses, the geometrical conditions, and the irradiation area (step Sa5). A patient skin dose distribution (dose distribution) on the patient model is generated based on the air kerma, the geometrical conditions, and the irradiation area (step Sa6).

If no dose distribution is stored in the storage unit 23 (step Sa7), the generated dose distribution is stored in the storage unit 23 (step Sa8). If a dose distribution is stored in the storage unit 23 (step Sa7), the generated dose distribution is added to the stored dose distribution (step Sa9). The resultant dose distribution is stored in the storage unit 23 (step Sa10). The dose distribution is displayed on the display unit 31, together with the patient model (step Sa11). If X-ray imaging of the object is not complete (step Sa12), the processing in steps Sa2 to Sa11 is repeated, except for the processing in steps Sa7 and Sa8.

Figure 7:
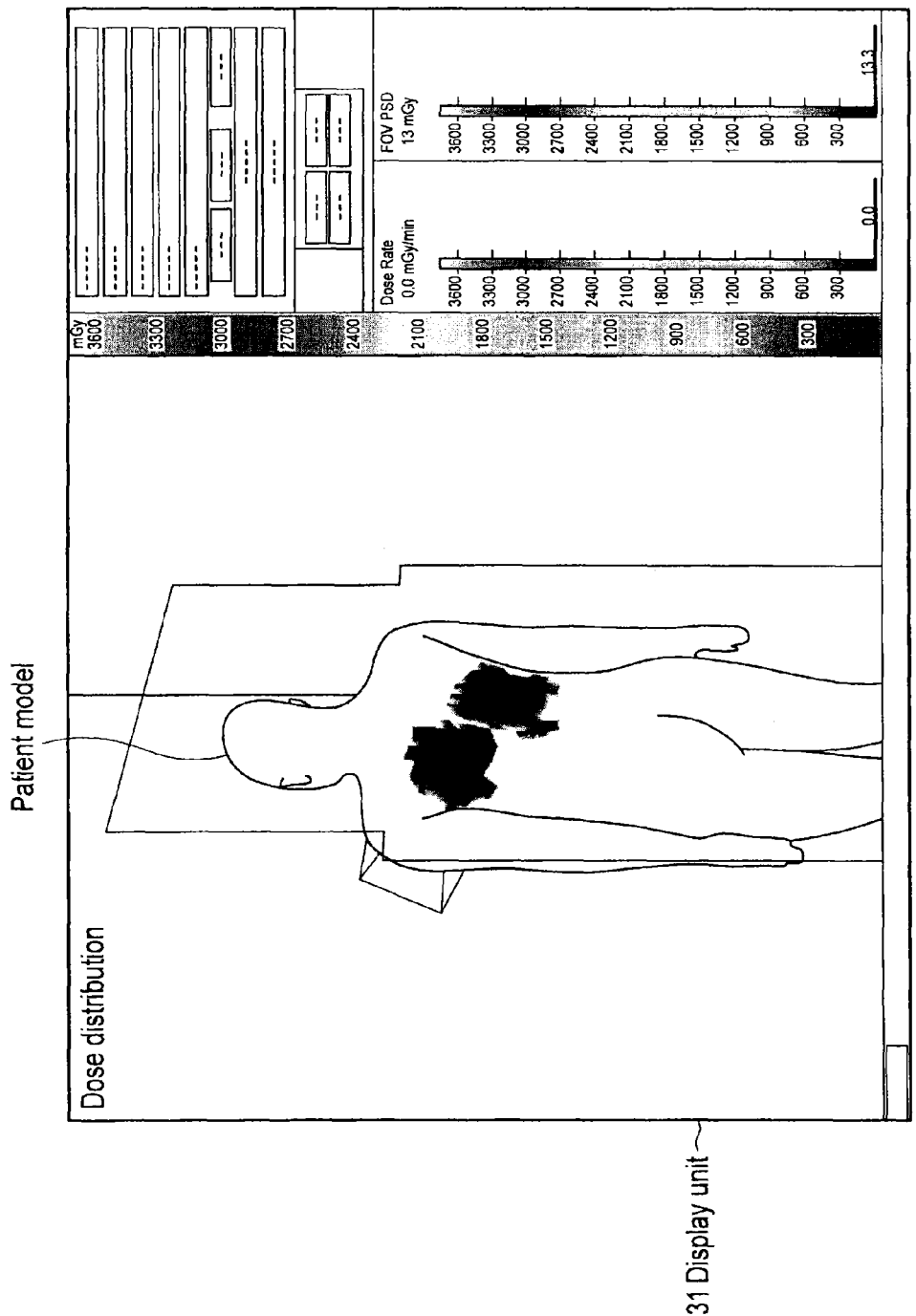
FIG. 7 is a view showing an example of the dose distribution displayed on a display unit together with a patient model according to this embodiment.

FIG. 7 is a view showing an example of the dose distribution displayed on the display unit 31, together with the patient model. As shown in FIG. 7, the dose distribution is displayed upon addition of dose distributions for the respective times of X-ray irradiation. Referring to FIG. 7, the dose distribution is indicated by shading in accordance with the magnitudes of patient skin doses. In practice, however, the dose distribution may be displayed in different hues corresponding to the magnitudes of patient skin doses.

FIG. 10 is a view showing an example of the dose distribution displayed on the display unit 31, together with a cylindrical dose distribution display model, patient model, X-ray tube model, X-ray detector model, and irradiated X-ray model. Note that the X-ray tube model, X-ray detector model, and irradiated X-ray model may be omitted. As shown in FIG. 10, the dose distribution is displayed on the cylindrical dose distribution display model upon addition of the dose distributions for the respective times of X-ray irradiation. Although the dose distribution is indicated by shading in accordance with the magnitudes of patient skin doses in FIG. 10, the dose distribution is displayed in different hues corresponding to the magnitudes of the patient skin doses in practice.

Figure 11:
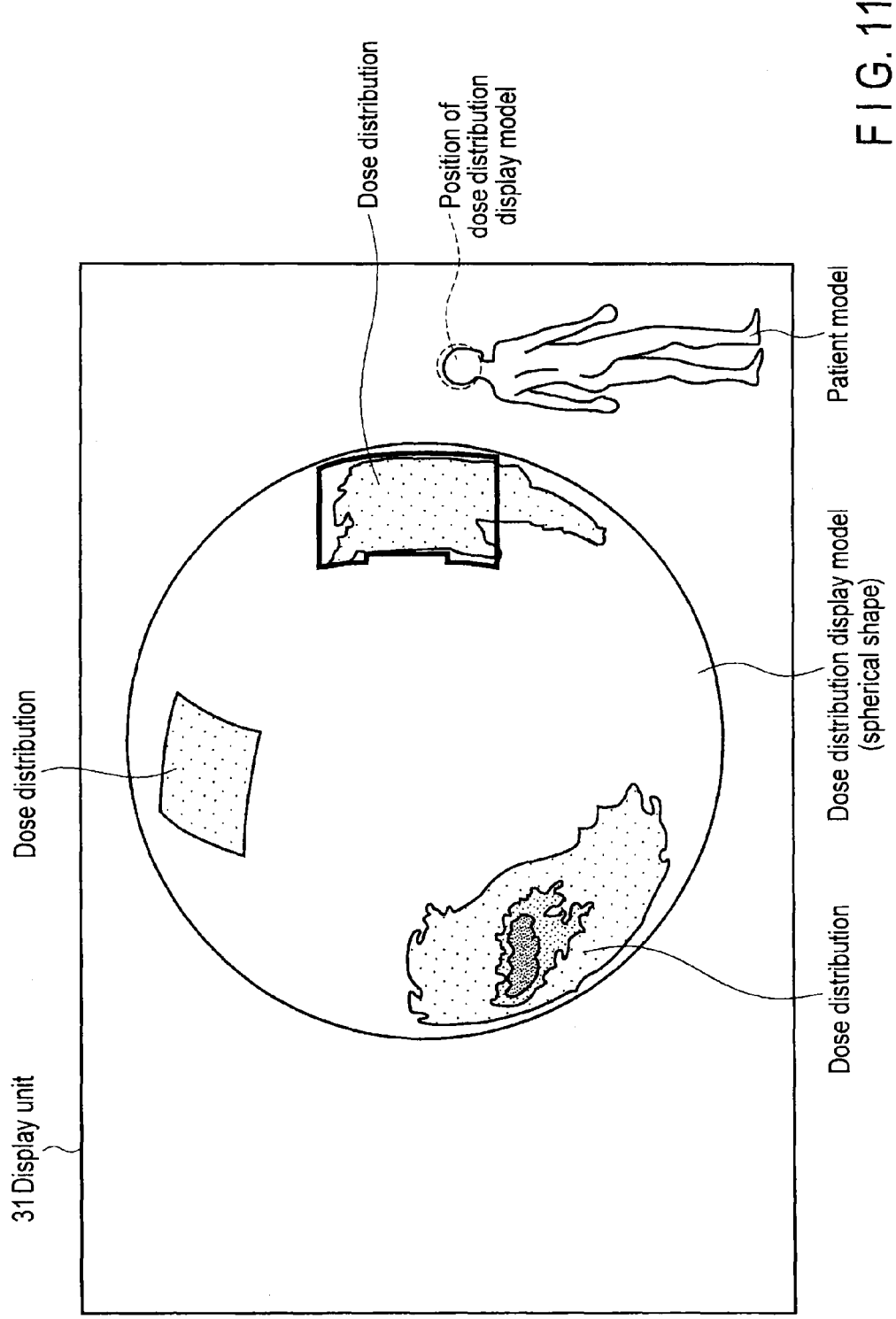
FIG. 11 is a view showing an example of the dose distribution displayed on the display unit together with a spherical dose distribution display model according to this embodiment.

FIG. 11 is a view showing an example of the dose distribution displayed on the display unit 31, together with a spherical dose distribution display model and a patient model. As shown in FIG. 11, the dose distribution is displayed on the spherical dose distribution display model upon addition of dose distributions for the respective times of X-ray irradiation. The position of the dose distribution display model is displayed on the patient model in FIG. 11 in a hue different from that of the patient model. Referring to FIG. 11, the dose distribution is displayed by shading corresponding to the magnitudes of the patient skin doses. In practice, however, the dose distribution may be displayed in different hues corresponding to the magnitudes of the patient skin doses.

(Modification)

A difference from this embodiment is that a plurality of area doses are decided by dividing a total area dose by the number of times of X-ray irradiation in a dose measurement period.

The storage unit 23 stores the number of times of X-ray irradiation in a dose measurement period, geometrical conditions for each time of X-ray irradiation, and an irradiation area.

The area dose decision unit 25 reads out the number of times of irradiation from the storage unit 23 for each dose measurement period, i.e., each dose readout period. The area dose decision unit 25 reads out a total area dose from the dosimeter 13 for each dose measurement period, i.e., a dose readout period. The area dose decision unit 25 decides an area dose by dividing the total area dose by the number of times of irradiation. The area dose decision unit 25 outputs the decided area doses to the dose distribution generation unit 27.

For the sake of simplicity, assume that the number of times of X-ray irradiation in a dose measurement period is five. Note that the number of times of X-ray irradiation is not limited to five and may be an arbitrary number of times of irradiation.

Figure 8:
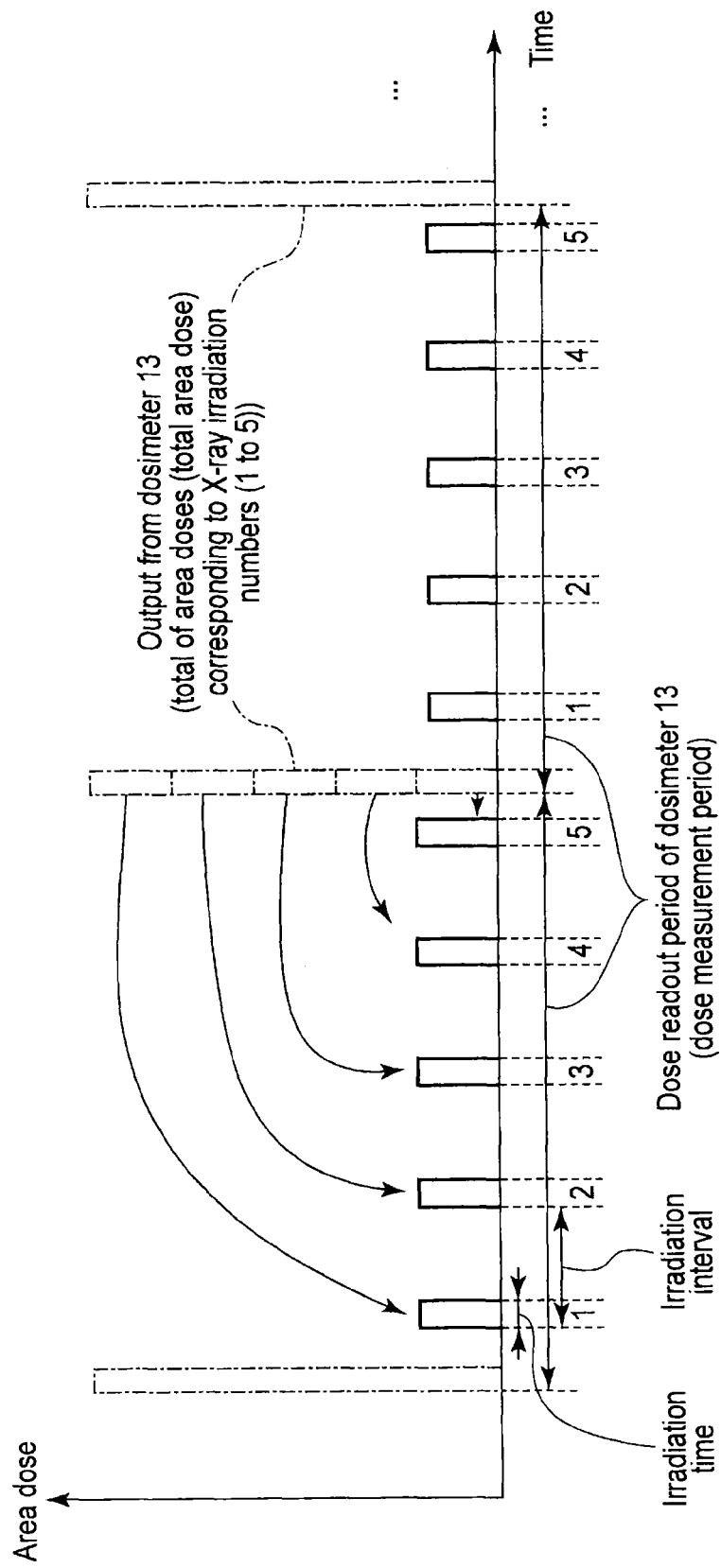
FIG. 8 is a graph showing an example obtained by dividing a total area dose into area doses for the respective times of X-ray generation (irradiation) in a dose measurement period according to the first modification of this embodiment.

FIG. 8 a graph showing an example obtained by dividing a total area dose into area doses for the respective times of X-ray generation (irradiation) in a dose measurement period. As shown in FIG. 8, a total area dose in a dose measurement period is divided into area doses for the respective times of X-ray generation (irradiation) in the dose measurement period.

(Dose Distribution Generation Function)

The dose distribution generation function is a function of deciding a plurality of area doses respectively corresponding to a plurality of times of X-ray irradiation (generation) in a dose measurement period by dividing a total area dose by the number of times of X-ray irradiation in the dose measurement period, and generating and displaying a dose distribution at a reference position based on the plurality of decided area doses, geometrical conditions, and an irradiation area. Processing concerning the dose distribution generation function (to be referred to as dose distribution generation processing hereinafter) will be described below.

Figure 9:
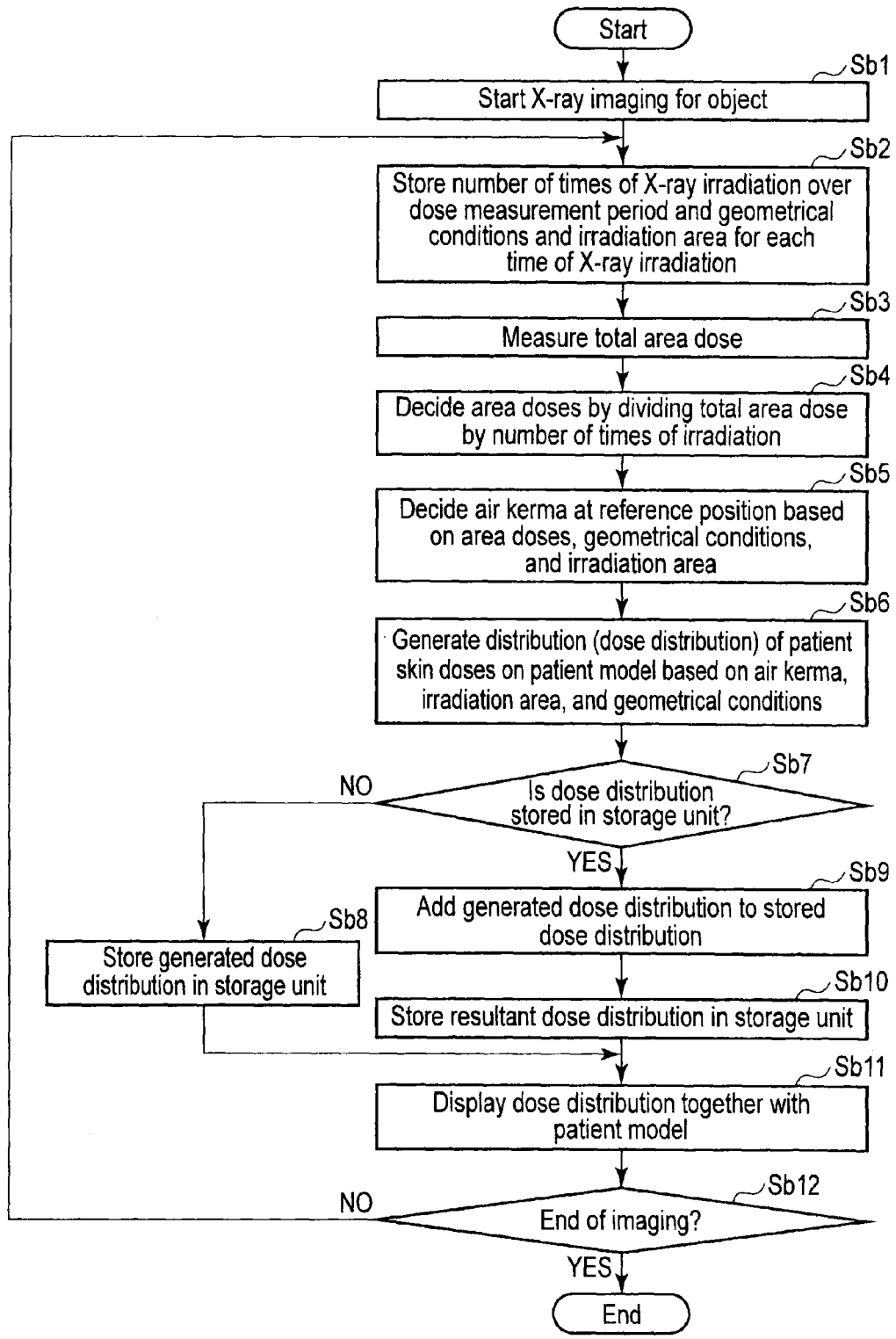
FIG. 9 is a flowchart showing an example of dose distribution generation processing according to the second modification of this embodiment.

FIG. 9 is a flowchart showing an example of a procedure for dose distribution generation processing.

X-ray imaging is started for an object (step Sb1). The storage unit 23 stores the number of times of X-ray irradiation over a dose measurement period and geometrical conditions and irradiation area for each time of X-ray irradiation (step Sb2). A total area dose is measured (step Sb3). Area doses are decided by dividing the total area dose by the number of times of irradiation (step Sb4). An air kerma at the reference position is decided based on the area doses, the geometrical conditions, and the irradiation area (step Sb5). A patient skin dose distribution (dose distribution) on the patient model is generated based on the air kerma, geometrical conditions, and an irradiation area (step Sb6).

If no dose distribution is stored in the storage unit 23 (step Sb7), the generated dose distribution is stored in the storage unit 23 (step Sb8). If a dose distribution is stored in the storage unit 23 (step Sb7), the generated dose distribution is added to the stored dose distribution (step Sb9). The resultant dose distribution is stored in the storage unit 23 (step Sb10). The dose distribution is displayed on the display unit 31, together with the patient model (step Sb11). If X-ray imaging of the object is not complete (step Sb12), the processing in steps Sb2 to Sb11 is repeated, except for the processing in steps Sb7 and Sb8.

With the above arrangement, the following effects can be obtained.

The X-ray diagnostic apparatus 1 according to this embodiment can decide a plurality of area doses respectively corresponding to a plurality of times of X-ray irradiation (generation) in a dose measurement period based on a total area dose and X-ray irradiation conditions, generate a dose distribution at a reference position based on the plurality of decided area doses, geometrical conditions, and an irradiation area, and accurately display the dose distribution. According to the X-ray diagnostic apparatus 1, this makes it possible to add dose distributions for the respective times of X-ray irradiation to the object and display the resultant dose distribution. In addition, the X-ray diagnostic apparatus 1 can calculate a patient skin dose in accordance with a change in X-ray irradiation position (rotational imaging and panning) during an X-ray irradiation period to the object, generate a useful dose distribution as an index for exposure of the object, and display the dose distribution. As described above, the X-ray diagnostic apparatus 1 can generate a dose distribution in real time by using the dosimeter (area dosimeter) 13 even with a change in irradiation region on the object. The X-ray diagnostic apparatus 1 according to this embodiment can accurately generate and display a dose distribution for each time of X-ray irradiation, in particular, when the imaging region changes for each time of X-ray irradiation.

In addition, the X-ray diagnostic apparatus 1 according to the modification of this embodiment can decide a plurality of area doses respectively corresponding to a plurality of times of X-ray irradiation (generation) in a dose measurement period by dividing a total area dose by the number of times of X-ray irradiation in the dose measurement period, generate a dose distribution at a reference position based on the plurality of decided area doses, geometrical conditions, and an irradiation area, and accurately display the dose distribution. This makes it possible to generate area doses more easily than in dose distribution generation processing in this embodiment. Therefore, this modification can further improve the real time performance. That is, the X-ray diagnostic apparatus 1 according to the modification can achieve a reduction in cost and further improve the responsiveness of the generation and display of a dose distribution when an imaging region for each time of X-ray irradiation remains the same (e.g., when an irradiation position does not change and X-ray irradiation conditions and geometrical conditions for each time of X-ray irradiation do not change).

In addition, each function according to this embodiment and this modification can be implemented by installing a program (dose distribution generation program) for executing dose distribution generation processing in a computer such as a workstation and loading it in the memory. In this case, the program which can cause the computer to execute this method can be distributed by being stored in storage media such as magnetic disks (floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
a support mechanism configured to movably support an X-ray tube configured to generate X-rays over a plurality of times in a predetermined period and an X-ray detector configured to detect X-rays transmitted through an object;
a bed including a top on which the object is placed;
a dosimeter configured to measure a total dose over the period;
a dose decision unit configured to decide a plurality of doses respectively corresponding to times of generation of the X-rays in the period based on the total dose and an X-ray irradiation condition;
a dose distribution generation unit configured to generate a dose distribution based on a position of the support mechanism, a position of the bed, and the doses; and
a display unit configured to display the dose distribution.

2. The apparatus according to claim 1, wherein the display unit is configured to display the dose distribution on a patient model.

3. The apparatus according to claim 1, wherein the display unit is configured to display the dose distribution on a cylindrical model.

4. The apparatus according to claim 1, wherein the display unit is configured to display the dose distribution on a spherical model.

5. The apparatus according to claim 1, wherein the X-ray irradiation condition includes a tube voltage applied to the X-ray tube, a tube current time product obtained by multiplying a tube current supplied to the X-ray tube by an irradiation time, the number of times of irradiation of the X-rays in the period, and a thickness of a predetermined filter inserted in an irradiation range of the X-rays, and
the dose decision unit is configured to decide the dose by further using an irradiation area at a reference position.

6. The apparatus according to claim 5, wherein the dose decision unit is configured to
decide a unit tube current time product and a dose per unit area based on the thickness of the filter and the tube voltage,
decide a dose rate indicating a rate of each of the doses to the total dose based on the unit tube current time product, the dose per unit area, the tube current time product, the irradiation range, and the number of times of irradiation, and
decide the doses based on each the dose rate, the total dose, and the irradiation area.

7. The apparatus according to claim 1, wherein the X-ray irradiation condition includes the number of times of irradiation of the X-rays in the period.

8. The apparatus according to claim 7, wherein the dose decision unit is configured to decide the doses by dividing the total dose by the number of times of irradiation.

9. The apparatus according to claim 1, wherein the dose distribution generation unit is configured to generate the dose distribution concerning a predetermined reference position by further using an irradiation area at the predetermined reference position.

10. A dose distribution generation method comprising:
generating X-rays over a plurality of times in a predetermined period;
measuring a total dose over the period;
deciding a plurality doses respectively corresponding to respective times of generation of the X-rays in the period based on the total dose and an X-ray irradiation condition;
generating a dose distribution based on a position of a support mechanism configured to support an X-ray tube configured to generate the X-rays, a position of a bed, and the doses; and
displaying the dose distribution.

* * * * *